United States Patent
Goraltchouk et al.

(10) Patent No.: US 8,216,273 B1
(45) Date of Patent: Jul. 10, 2012

(54) SELF-RETAINERS WITH SUPPORTING STRUCTURES ON A SUTURE

(75) Inventors: Alexei Goraltchouk, Richmond BC (CA); Lev Drubetsky, Coquitlam BC (CA); Gerald F. Cummings, Port Moody BC (CA); Robert A. Herrmann, Vancouver BC (CA); Alexander Naimagon, Richmond BC (CA)

(73) Assignee: Ethicon, Inc., Somerville, NJ (US)

( * ) Notice: Subject to any disclaimer, the term of this patent is extended or adjusted under 35 U.S.C. 154(b) by 601 days.

(21) Appl. No.: 12/392,945

(22) Filed: Feb. 25, 2009

Related U.S. Application Data (60) Provisional application No. 61/031,274, filed on Feb. 25, 2008.

(51) Int. Cl.
 *A61B 17/04* (2006.01)
(52) U.S. Cl. .................................................. 606/228
(58) Field of Classification Search .......... 606/228–232, 606/219
 See application file for complete search history.

(56) References Cited

U.S. PATENT DOCUMENTS

| | | |
|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederrer |
| 1,321,011 A | 11/1919 | Cottes |
| 1,558,037 A | 10/1925 | Morton |
| 1,728,316 A | 9/1929 | Wachenfeldt |
| 1,886,721 A | 11/1932 | O'Brien |
| 2,201,610 A | 5/1940 | Dawson |
| 2,232,142 A | 2/1941 | Schumann |
| 2,254,620 A | 9/1941 | Miller |
| 2,355,907 A | 8/1944 | Cox |
| 2,421,193 A | 5/1947 | Gardner |
| 2,472,009 A | 5/1949 | Gardner |
| 2,572,936 A | 10/1951 | Kulp et al. |
| 2,684,070 A | 7/1954 | Kelsey |
| 2,779,083 A | 1/1957 | Eaton |
| 2,814,296 A | 11/1957 | Everett |
| 2,817,339 A | 12/1957 | Sullivan, Norman |
| 2,866,256 A | 12/1958 | Matlin, Nathaniel |
| 2,910,067 A | 10/1959 | White, John |
| 2,988,028 A | 6/1961 | Alcamo |

(Continued)

FOREIGN PATENT DOCUMENTS

BE 1014364 9/2003

(Continued)

OTHER PUBLICATIONS

Bellin et al., "Polymeric triple-shape materials", Proceedings of the National Academy of Sciences of the United States of America Nov. 28, 2006; 2103(48):18043-18047.

(Continued)

*Primary Examiner* — Julian Woo (57) ABSTRACT

In embodiments of the invention, a manufacturing process produces and an. Article produced has a self-retaining suture wherein a force is used to squeeze the suture causing retainers to form out of material from the suture body. In an embodiment of the invention, fins are formed between the retainers and the suture body, wherein said fins support the retainers. In another embodiment, retainer stops are provided in order to prevent the retainer from settling back in the body of the suture.

5 Claims, 7 Drawing Sheets

U.S. PATENT DOCUMENTS

| | | |
|---|---|---|
| 3,003,155 A | 10/1961 | Mielzynski |
| 3,068,869 A | 12/1962 | Shelden, Charles |
| 3,068,870 A | 12/1962 | Levin, Abraham |
| 3,123,077 A | 3/1964 | Alcamo, John |
| 3,166,072 A | 1/1965 | Sullivan |
| 3,206,018 A | 9/1965 | Lewis et al. |
| 3,209,754 A | 10/1965 | Brown |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | Le Roy |
| 3,494,006 A | 2/1970 | Brumlik |
| 3,525,340 A | 8/1970 | Gilbert |
| 3,527,223 A | 9/1970 | Shein |
| 3,545,608 A | 12/1970 | Berger et al. |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,646,615 A | 3/1972 | Ness |
| 3,683,926 A | 8/1972 | Suzuki |
| 3,716,058 A | 2/1973 | Tanner, Jr. |
| 3,825,010 A | 7/1974 | McDonald |
| 3,833,972 A | 9/1974 | Brumlik |
| 3,918,455 A | 11/1975 | Coplan |
| 3,951,261 A | 4/1976 | Mandel et al. |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 4,006,747 A | 2/1977 | Kronenthal et al. |
| 4,069,825 A | 1/1978 | Akiyama |
| 4,073,298 A | 2/1978 | Le Roy |
| 4,198,734 A | 4/1980 | Brumlik |
| 4,204,541 A | 5/1980 | Kapitanov |
| 4,259,959 A | 4/1981 | Walker |
| 4,300,424 A | 11/1981 | Flinn et al. |
| 4,313,448 A | 2/1982 | Stokes |
| 4,316,469 A | 2/1982 | Kapitanov |
| 4,317,451 A | 3/1982 | Cerwin et al. |
| 4,428,376 A | 1/1984 | Mericle |
| 4,430,998 A | 2/1984 | Harvey et al. |
| 4,434,796 A | 3/1984 | Karapetian et al. |
| 4,454,875 A | 6/1984 | Pratt et al. |
| 4,467,805 A | 8/1984 | Fukuda |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,548,202 A | 10/1985 | Duncan |
| 4,553,544 A | 11/1985 | Nomoto et al. |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,719,917 A | 1/1988 | Barrows et al. |
| 4,741,330 A | 5/1988 | Hayhurst |
| 4,776,337 A | 10/1988 | Palmaz |
| 4,832,025 A | 5/1989 | Coates |
| 4,841,960 A | 6/1989 | Garner |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,905,367 A | 3/1990 | Pinchuk et al. |
| 4,930,945 A | 6/1990 | Arai et al. |
| 4,946,468 A | 8/1990 | Li |
| 4,948,444 A | 8/1990 | Schutz et al. |
| 4,950,285 A | 8/1990 | Wilk |
| 4,968,315 A | 11/1990 | Gatturna |
| 4,976,715 A | 12/1990 | Bays et al. |
| 4,981,149 A | 1/1991 | Yoon et al. |
| 4,994,073 A | 2/1991 | Green |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,101,968 A | 4/1992 | Henderson et al. |
| 5,102,418 A | 4/1992 | Granger et al. |
| 5,102,421 A | 4/1992 | Anspach, Jr. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,156,788 A | 10/1992 | Chesterfield et al. |
| 5,176,692 A | 1/1993 | Wilk et al. |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,269,783 A | 12/1993 | Sander |
| 5,282,832 A | 2/1994 | Toso et al. |
| 5,292,326 A | 3/1994 | Green et al. |
| 5,306,290 A | 4/1994 | Martins et al. |
| 5,320,629 A | 6/1994 | Noda et al. |
| 5,330,488 A | 7/1994 | Goldrath |
| 5,330,503 A | 7/1994 | Yoon |
| 5,341,922 A | 8/1994 | Cerwin et al. |
| 5,342,376 A | 8/1994 | Ruff |
| 5,352,515 A | 10/1994 | Jarrett et al. |
| 5,354,298 A | 10/1994 | Lee et al. |
| 5,358,511 A | 10/1994 | Gatturna et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 4,311,002 A | 5/1995 | Dipalma, Michele et al. |
| 5,411,523 A | 5/1995 | Goble |
| 5,414,988 A | 5/1995 | DiPalma et al. |
| 5,425,746 A | 6/1995 | Proto et al. |
| 5,425,747 A | 6/1995 | Brotz |
| 5,450,860 A | 9/1995 | O'Connor |
| 5,462,561 A | 10/1995 | Voda |
| 5,464,427 A | 11/1995 | Curtis et al. |
| 5,472,452 A | 12/1995 | Trott |
| 5,480,403 A | 1/1996 | Lee et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,691 A | 5/1996 | Branch |
| 5,522,845 A | 6/1996 | Wenstrom, Jr. |
| 5,531,761 A | 7/1996 | Yoon |
| 5,533,982 A | 7/1996 | Rizk et al. |
| 5,536,582 A | 7/1996 | Prasad et al. |

| | | |
|---|---|---|
| 5,546,957 A | 8/1996 | Heske |
| 5,554,171 A | 9/1996 | Gatturna et al. |
| 5,566,822 A | 10/1996 | Scanlon |
| 5,571,175 A | 11/1996 | Vanney et al. |
| 5,573,543 A | 11/1996 | Akopov et al. |
| 5,584,859 A | 12/1996 | Brotz |
| 5,601,557 A | 2/1997 | Hayhurst |
| 5,626,590 A | 5/1997 | Wilk |
| 5,643,295 A | 7/1997 | Yoon |
| 5,643,319 A | 7/1997 | Green et al. |
| 5,662,714 A | 9/1997 | Charvin et al. |
| 5,669,935 A | 9/1997 | Rosenman et al. |
| 5,683,417 A | 11/1997 | Cooper |
| 5,697,976 A | 12/1997 | Chesterfield et al. |
| 5,702,462 A | 12/1997 | Oberlander |
| 5,709,692 A | 1/1998 | Mollenauer et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,779,719 A | 7/1998 | Klein et al. |
| 5,782,864 A | 7/1998 | Lizardi |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,931,855 A | 8/1999 | Buncke |
| 5,935,138 A | 8/1999 | McJames, II et al. |
| 5,938,668 A | 8/1999 | Scirica et al. |
| 5,950,633 A | 9/1999 | Lynch et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,056,778 A | 5/2000 | Grafton et al. |
| 6,083,244 A | 7/2000 | Lubbers et al. |
| 6,102,947 A | 8/2000 | Gordon |
| 6,146,407 A | 11/2000 | Krebs |
| 6,163,948 A | 12/2000 | Esteves et al. |
| 6,165,203 A | 12/2000 | Krebs |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,206,908 B1 | 3/2001 | Roby |
| 6,241,747 B1 | 6/2001 | Ruff |
| 6,251,143 B1 | 6/2001 | Schwartz et al. |
| 6,264,675 B1 | 7/2001 | Brotz |
| 6,270,517 B1 | 8/2001 | Brotz |
| 6,315,788 B1 | 11/2001 | Roby |
| 6,334,865 B1 | 1/2002 | Redmond et al. |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| RE37,963 E | 1/2003 | Thal |
| 6,506,190 B1 | 1/2003 | Walshe |
| 6,514,265 B2 | 2/2003 | Ho et al. |
| 6,554,802 B1 | 4/2003 | Pearson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,623,492 B1 | 9/2003 | Berube et al. |
| 6,626,930 B1 | 9/2003 | Allen et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,712,830 B2 | 3/2004 | Esplin |
| 6,726,705 B2 | 4/2004 | Peterson et al. |
| 6,746,458 B1 | 6/2004 | Cloud |
| 6,773,450 B2 | 8/2004 | Leung et al. |
| 6,783,554 B2 | 8/2004 | Amara et al. |
| 6,818,010 B2 | 11/2004 | Eichhorn et al. |
| 6,848,152 B2 | 2/2005 | Genova et al. |
| 6,893,452 B2 | 5/2005 | Jacobs |
| 6,905,484 B2 | 6/2005 | Buckman et al. |
| 6,911,035 B1 | 6/2005 | Blomme |
| 6,960,233 B1 | 11/2005 | Berg et al. |
| 6,981,983 B1 | 1/2006 | Rosenblatt et al. |
| 6,984,241 B2 | 1/2006 | Lubbers et al. |
| 6,991,643 B2 | 1/2006 | Saadat |
| 7,021,316 B2 | 4/2006 | Leiboff |
| 7,048,748 B1 | 5/2006 | Ustuner |
| 7,056,331 B2 | 6/2006 | Kaplan et al. |
| 7,056,333 B2 | 6/2006 | Walshe |
| 7,070,610 B2 | 7/2006 | Im et al. |
| 7,083,637 B1 | 8/2006 | Tannhauser |
| 7,112,214 B2 | 9/2006 | Peterson et al. |
| D532,107 S | 11/2006 | Peterson et al. |
| 7,138,441 B1 | 11/2006 | Zhang |
| 7,144,412 B2 | 12/2006 | Wolf et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et |
| 7,225,512 B2 | 6/2007 | Genova et al. |
| 7,226,468 B2 | 6/2007 | Ruff |
| 7,232,447 B2 | 6/2007 | Gellman et al. |
| 7,850,894 B2 * | 12/2010 | Lindh, Sr. et al. ............ 606/228 |
| 2001/0011187 A1 | 8/2001 | Pavcnik et al. |
| 2001/0039450 A1 | 11/2001 | Pavcnik et al. |
| 2001/0044637 A1 | 11/2001 | Jacobs et al. |
| 2001/0051815 A1 | 12/2001 | Esplin |
| 2002/0022861 A1 | 2/2002 | Jacobs et al. |
| 2002/0029066 A1 | 3/2002 | Foerster |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0173807 A1 | 11/2002 | Jacobs |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1 | 8/2003 | Morency et al. |
| 2003/0158604 A1 | 8/2003 | Cauthen, III et al. |
| 2003/0167072 A1 | 9/2003 | Oberlander |
| 2003/0204195 A1 | 10/2003 | Keane et al. |
| 2003/0229361 A1 | 12/2003 | Jackson |
| 2004/0010275 A1 | 1/2004 | Jacobs et al. |
| 2004/0010276 A1 | 1/2004 | Jacobs et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0060409 A1 | 4/2004 | Leung et al. |
| 2004/0060410 A1 | 4/2004 | Leung et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |

| | | |
|---|---|---|
| 2004/0138683 A1 | 7/2004 | Shelton et al. |
| 2004/0153153 A1 | 8/2004 | Elson et al. |
| 2004/0186487 A1 | 9/2004 | Klein et al. |
| 2004/0193217 A1 | 9/2004 | Lubbers et al. |
| 2004/0226427 A1 | 11/2004 | Trull et al. |
| 2004/0237736 A1 | 12/2004 | Genova et al. |
| 2004/0254609 A1 | 12/2004 | Esplin |
| 2004/0260340 A1 | 12/2004 | Jacobs et al. |
| 2004/0265282 A1 | 12/2004 | Wright et al. |
| 2005/0004602 A1 | 1/2005 | Hart et al. |
| 2005/0033367 A1 | 2/2005 | Leung et al. |
| 2005/0059984 A1 | 3/2005 | Chanduszko et al. |
| 2005/0065533 A1 | 3/2005 | Magen et al. |
| 2005/0070959 A1 | 3/2005 | Cichocki |
| 2005/0080455 A1 | 4/2005 | Schmieding et al. |
| 2005/0119694 A1 | 6/2005 | Jacobs et al. |
| 2005/0125020 A1 | 6/2005 | Meade et al. |
| 2005/0125035 A1 | 6/2005 | Cichocki |
| 2005/0171561 A1 | 8/2005 | Songer et al. |
| 2005/0177190 A1 | 8/2005 | Zamierowski |
| 2005/0182445 A1 | 8/2005 | Zamierowski |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen et al. |
| 2006/0030884 A1 | 2/2006 | Yeung et al. |
| 2006/0036266 A1 | 2/2006 | Sulamanidze et al. |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0122608 A1 | 6/2006 | Fallin et al. |
| 2006/0135994 A1 | 6/2006 | Ruff et al. |
| 2006/0135995 A1 | 6/2006 | Ruff et al. |
| 2006/0142784 A1 | 6/2006 | Kontos |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235447 A1 | 10/2006 | Walshe |
| 2006/0235516 A1 | 10/2006 | Cavazzoni |
| 2006/0253126 A1 | 11/2006 | Bjerken et al. |
| 2006/0276808 A1 | 12/2006 | Arnal et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088391 A1 | 4/2007 | McAlexander et al. |
| 2007/0135840 A1 | 6/2007 | Schmieding |
| 2007/0135843 A1 | 6/2007 | Burkhart |
| 2007/0187861 A1 | 8/2007 | Genova et al. |
| 2007/0208377 A1 | 9/2007 | Kaplan et al. |
| 2007/0219587 A1 | 9/2007 | Accardo |
| 2007/0224237 A1 | 9/2007 | Hwang et al. |
| 2007/0225761 A1 | 9/2007 | Shetty |
| 2007/0233188 A1 | 10/2007 | Hunt et al. |
| 2007/0239206 A1 | 10/2007 | Shelton et al. |
| 2008/0009888 A1 | 1/2008 | Ewers et al. |
| 2008/0058869 A1 | 3/2008 | Stopek et al. |
| 2008/0195147 A1 | 8/2008 | Stopek |
| 2008/0312688 A1 | 12/2008 | Nawrocki et al. |
| 2009/0018577 A1 | 1/2009 | Leung et al. |
| 2009/0043336 A1 | 2/2009 | Yuan et al. |

FOREIGN PATENT DOCUMENTS

| | | |
|---|---|---|
| DE | P 1 810 800 | 6/1970 |
| DE | 43 02 895 | 8/1994 |
| DE | 19618891 | 4/1997 |
| DE | 19833703 | 2/2000 |
| DE | 10 2005 004317 | 6/2006 |
| EP | 0428253 | 5/1991 |
| EP | 0464479 | 1/1992 |
| EP | 0513736 | 11/1992 |
| EP | 0558993 | 9/1993 |
| EP | 0574707 | 12/1993 |
| EP | 0576337 | 12/1993 |
| EP | 0612504 | 8/1994 |
| EP | 0664198 | 7/1995 |
| EP | 0673624 | 9/1995 |
| EP | 0705567 | 4/1996 |
| EP | 0755656 | 1/1997 |
| EP | 826337 | 3/1998 |
| EP | 0916310 | 5/1999 |
| EP | 0960600 | 12/1999 |
| EP | 1075843 | 2/2001 |
| EP | 1525851 | 4/2005 |
| EP | 1 726 317 | 11/2006 |
| FR | 2619129 | 2/1989 |
| FR | 2693108 | 1/1994 |
| GB | 267007 | 3/1927 |
| GB | 1091282 | 11/1967 |
| GB | 1506362 | 4/1978 |
| JP | 63288146 | 11/1988 |
| WO | WO 88/09157 | 12/1988 |
| WO | WO 89/05618 | 6/1989 |
| WO | WO 90/09149 | 8/1990 |
| WO | WO 9852473 | 11/1998 |
| WO | WO 98/55031 | 12/1998 |
| WO | WO 9921488 | 5/1999 |
| WO | WO 99/33401 | 7/1999 |
| WO | WO 99/62431 | 12/1999 |
| WO | WO 00/51658 | 9/2000 |
| WO | WO 01/06952 | 2/2001 |
| WO | WO 03/001979 | 1/2003 |
| WO | WO 03/017850 | 3/2003 |
| WO | WO 03/045255 | 6/2003 |
| WO | WO 03/077772 | 9/2003 |
| WO | WO 03/092758 | 11/2003 |
| WO | WO 03/103972 | 12/2003 |
| WO | WO 03/105703 | 12/2003 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/112853 | 12/2004 |
| WO | WO 2005/096955 | 10/2005 |
| WO | WO 2005/096956 | 10/2005 |
| WO | WO 2006/005144 | 1/2006 |
| WO | WO 2006/012128 | 2/2006 |
| WO | WO 2006/061868 | 6/2006 |
| WO | WO 2006/079469 | 8/2006 |
| WO | WO 2006/099703 | 9/2006 |
| WO | WO 2007/005291 | 1/2007 |
| WO | WO 2007005296 | 1/2007 |
| WO | WO 2007/053812 | 5/2007 |
| WO | WO 2007/112024 | 10/2007 |
| WO | WO 2007/133103 | 11/2007 |

OTHER PUBLICATIONS

Bunnell, S., "Gig pull-out suture for tendons." J Bone Joint Surg Am. Jul. 1954;36-A(4):850-1.

Dattillo, Jr., Philip Paul, "Knotless Bi-directional Barbed Absorbable Surgical Suture", Dissertation submitted to the Graduate Faculty of North Carolina State University Textile Management and Technology Nov. 2002, 75 pages.

Delorenzi, C.L., "Barbed Sutures: Rationale and Technique." Aesthetic Surg J. Mar. 26, 2006(2): 223-229.

Han, Hongtao et al., "Mating and Piercing Micromechanical Structures for Surface Bonding Applications", Proceedings of the 1991 Micro Electro Mechanical Systems (MEMS '91), An Investigation of Micro Structures, Sensors, Actuators, Machines and Robots, Feb. 1991, pp. 253-258.

Ingle, Nilesh p. et al., "Barbed Suture Anchoring Strength: Applicability to Dissimilar Polymeric Materials", College of Textiles, North Carolina State University, 7$^{th}$ World Biomaterials Congress 2004, 1 page.

Ingle, Nilesh p. et al., "Testing the Tissue-holding Capacity of Barbed Sutures", College of Textiles, North Carolina State University, Fiber Science—The Next Generation Oct. 17-19 2005, New Jersey Institute of Technology, Newark, NJ, 4 pages.

International Search Report for PCT/US2007/074658 dated Jun. 12, 2007, 4 pages.

International Search Report for PCT/US2008/060127 dated Sep. 23, 2008, 8 pages.

International Search Report for PCT/US2008/0064921 dated Nov. 19, 2008, 8 pages.

International Search Report for PCT/US2008/075849 dated Mar. 18, 2009, 7 pages.

Jennings et al., "A new technique in primary tendon repair." Surg Gynecol Obstet Nov. 1952;95(5):597-600.

Kaminer, M. et al., "ContourLift™:A New Method of Minimally Invasive Facial Rejuvenation", Cosmetic Dermatology Jan. 2007; 20(1): 29-35.

Kelch et al., "Shape-memory Polymer Networks from Olio[(∈-hydroxycaproate)-co-glycolate]dimethacrylates and Butyl Acrylate with Adjustable Hydrolytic Degradation Rate", Biomacromolecules 2007;8(3):1018-1027.

Leung, J. et al., "Performance Enhancement of a Knotless Suture via Barb Geometry Modifications", 7$^{th}$ World Biomaterials Congress 2004, 1 page.

Leung, J. et al., "Barbed, Bi-directional Medical Sutures: Biomechanical Properties and Wound Closure Efficacy Study", 2002 Society for Biomaterials 28$^{th}$ Annual Meeting Transactions, 1 page.

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al., "Endovascular Aaa Exclusion: Will Stents With Hooks and Barbs Prevent Stent-Graft Migration?", Journal of Endovascular Surgery 1998; 5; 310-317.

Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.

Mason, M.L., "Primary and secondary tendon suture. A discussion of the significance of technique in tendon surgery." Surg Gynecol Obstet 70 (1940).

McKee, G.K., "Metal anastomosis tubes in tendon suture." The Lancet, May 26, 1945, 659-660.

McKenzie, A.R."An Experimental Multiple Barbed Suture for the Long Flexor Tendons of the Palm and Fingers." J Bone Joint Surg. 49B-(3): 440. 1967.

Moran et al., "Bidirectional-Barbed Sutured Knotless Running Anastomosis v Classic van Velthovan in a Model System", Journal of Endourology Oct. 2007; 21(10); 1175-1177.

Murtha et al., "Evaluation of a Novel Technique for Wound Closure Using a Barbed Suture", Journal of the American Society of Plastic Surgeons 2006; 117(6); 1769-1780.

Paul, Malcolm, "Using Barbed Sutures in Open/Subperiosteal Midface Lifting", Aesthetic Surgery Journal Nov./Dec. 2006; 26(6):725-732.

Potenza, Austin, "Tendon Healing Within the Flexor Digital Sheath in the Dog: An Experimental Study", Journal of Bone & Joint Surgery Jan. 1962; 44A(1):49-64.

Pulvertaft, "Suture Materials and Tendon Junctures", American Journal of Surgery Mar. 1965; 109:346-352.

Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2 pages, 2004.

Ruff, Gregory, "Technique and Uses for Absorbable Barbed Sutures", Aesthetic Surgery Journal Sep./Oct. 2006; 26:620-628.

Singapore Search Report for Singapore Patent Application No. 200702625-5 dated Nov. 26, 2008, 8 pages.

Singapore Search Report for Singapore Patent Application No. 200702350-0 dated Nov. 26, 2008, 7 pages.

Singapore Search Report for Singapore Patent Application No. 200703688-2 dated Nov. 26, 2008, 8 pages.

Sulamanidze, MD, M.A., et al., "Removal of Facial Soft Tissue Ptosis with Special Threads." Dermatol Surg 2002; 28; pp. 367-371.

Szarmach, Robin et al., "An Expanded Surgical Suture and Needle Evaulation and Selection Program by a Healthcare Resource Management Group Purchasing Organization", Journal of Long-Term Effects of Medical Implants 2003; 13(3); 155-170.

Verdan, Claude, "Primary Repair of Flexor Tendons", Journal of Bone and Joint Surgery Jun. 1960; 42(4):647-657.

* cited by examiner

SELF-RETAINERS WITH SUPPORTING STRUCTURES ON A SUTURE

FIELD OF THE INVENTION

The present invention relates to suture and retainer geometries and methods of forming retainers on sutures.

BACKGROUND OF THE INVENTION

Sutures are commonly used for closing or binding together wounds in human or animal tissue, such as skin, muscles, tendons, internal organs, nerves, and blood vessels. Sutures can be formed from non-absorbable material such as silk, nylon, polypropylene, or cotton, or alternatively sutures can be formed from bio-absorbable material such as, but not limited to, homopolymers and/or copolymers of glycolide, lactide, p-dioxanone and ε-caprolactone.

Self-retaining sutures (often referred to as "barbed sutures") differ from conventional sutures in that such self-retaining sutures possess numerous retainers (often barbs) which anchor into the surrounding tissue following deployment, thereby eliminating the need to tie knots to affix adjacent tissues together. Self-retaining sutures have been described in, for example, U.S. Pat. No. 6,848,152 and European Patent No. 1 075 843. All patents, patent applications, patent publications and other publications identified throughout are incorporated by reference. Such retainers protrude from the suture periphery and are arranged to allow passage of the self-retaining suture when drawn in one direction (with respect to the direction of protrusion of the retainer) through tissue but resist movement of the self-retaining suture when drawn in the opposite direction. Retainers can reduce slippage of the suture at least in a direction along the suture and can optionally obviate knotting of the suture.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described in the context of barbed retainers in U.S. Pat. Nos. 5,931,855 and 6,241,747). Although any number of sequential or intermittent configurations of retainers are possible, the most common form involves a needle at one end, followed by barbs projecting "away" from the needle until the transition point (often the midpoint) of the suture is reached; at the transition point the configuration of barbs reverses itself 180° (i.e., the barbs are now facing in the opposite direction) along the remaining length of the suture thread before attaching to a second needle at the opposite end.

Single-directional self-retaining sutures can include an end that is pointed to allow penetration and passage through tissue when drawn by the end and an opposite end that includes, for example, an anchor for engaging tissue at the initial insertion point to limit movement of the suture. Alternatively, bi-directional self-retaining sutures can include retainers grouped and extending in one direction along one portion of the suture and opposing retainers grouped and extending in an opposing direction along another portion of the suture. When implanted so that both groups of retainers are engaging tissue, the retainers can resist movement of the suture through tissue in either direction.

A surgeon may use a surgical needle with an attached suture (which can be a smooth monofilament or can be a multi-filament) to pierce the tissue alternately on opposing faces of a wound to sew the wound closed. Techniques for placement of self-retaining sutures in tissue to close or bind together wounds can include threading the self-retaining suture in straight-line patterns such as a zigzag pattern, and curvilinear patterns such as alpha, sinusoidal, and corkscrew patterns. A surgeon may also use self-retaining sutures to position and support tissue where there is no wound in procedures such as cosmetic surgery of the face, neck, abdominal or thoracic region among others.

More specifically, self-retaining sutures can be used in superficial and deep surgical procedures in humans and animals for closing wounds, repairing traumatic injuries or defects, joining tissues together (bringing severed tissues into approximation, closing an anatomical space, affixing single or multiple tissue layers together, creating anastomoses between two hollow (luminal) structures, adjoining tissues, attaching or reattaching tissues to the proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures typically consist of a filamentous suture thread attached to a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US2004-0088003). Classically, the needle is advanced through the desired tissue on one side of the wound and then through the adjacent side of the wound to form a "loop" which is then completed by tying a knot in the suture.

Sutures materials are broadly classified as being bioabsorbable (i.e., break down completely in the body over time), such as those composed of catgut, glycolic acid polymers and copolymers, lactic acid polymers and copolymers, and polyether-esters such as polyglycolide or lactide copolymers with glycols (such as methylene or ethylene ether glycol) or polyethers such as polyethylene glycol or polymethylene glycol; or as being non-absorbable (permanent; nondegradable), such as those made of polyamide, polytetrafluoroethylene, polyethylene terephthalate, polyurethane, polyether-esters such as polybutylene or ethylene terephthalate based copolymers with glycols (such as methylene or ethylene ether glycol) or polyethers such as polyethylene glycol or polymethylene glycol, metal alloys, metal (e.g., stainless steel wire), polypropylene, polyethelene, silk, and cotton. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses.

Self-retaining sutures are designed for engaging tissue when the suture is pulled in a direction other than that in which it was originally deployed in the tissue. Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. One of the earlier patents describing a barbed suture is U.S. Pat. No. 3,716,058, which discloses a suture having one or more relatively rigid barbs at its opposite ends; the presence of the barbs just at the ends of the suture would limit the barbs' effectiveness. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures by cutting barbs into a suture body have been described in, for example, U.S. Pat. Nos. 6,848,152 and 7,225,512. Methods of manufacturing sutures with frustoconical retainers have also been described, for example, in European Patent No. 1 075 843 and U.S. Patent Publication No. US2007-0038429.

BRIEF SUMMARY OF THE INVENTION

In one aspect, there is provided a method of forming a self-retaining suture which includes providing an elongated body and forming a tissue retainer by deforming the elongated body such that the tissue retainer protrudes outward from the outer circumference of the elongated body. In certain embodiments, the elongated body is deformed by pinching the elongated body. In certain embodiments, the method further includes forming a fin between the tissue retainer and the elongated body. In certain embodiments, the method further includes forming a slot in the fin of the tissue retainer.

In another aspect, there is provided a method of forming a self-retaining suture which includes extruding an elongated body and applying pressure to one or more local areas to deform the elongated body such that one or more tissue retainers are formed; wherein the tissue retainers protrude outward from the outer circumference at the one or more local areas. In certain embodiments, the pinching forms a fin between the tissue retainer and the elongated body. In certain of these embodiments, the method further includes forming a slot in the fin of the tissue retainer.

In another aspect, there is provided a self-retaining suture having one or more filament wherein the one or more filament has an elongated body; one or more tissue retainers formed by applying pressure to the elongated body such that the tissue retainers protrude outward from the elongated body; and at least one fin. In this aspect, the at least one fin corresponds with the area of the elongated body where the pressure was applied and is located between one or more respective tissue retainers and the elongated body, and supports the respective one or more retainers. In certain embodiments, the pressure applied pinches the elongated body to form the retainer. In certain further embodiments, the fin holds the retainer in position. In certain embodiments, the self-retaining suture further includes a slot in the at least one fin. In certain of these embodiments, cut fin holds the retainer in position while allowing some movement. In certain embodiments, the slot allows the tissue retainer to compress toward the suture body during insertion of the suture into tissue.

In yet another aspect, there is provided a self-retaining suture system having an elongated body, a retainer projecting form the elongated body, and a retainer stop located between the elongated body and the retainer, where in the retainer stop prevents the retainer from settling back against the elongated body. In certain embodiments, the suture system further includes a fin joining the elongated body and the retainer, and in which the retainer stop is formed in the fin. In certain embodiments, the retainer stop can move to a position between the retainer and the elongated body when the elongated body is bent in order to prevent the retainer from settling back against the elongated body. In certain embodiments, the suture system further includes a fin supporting the retainer from the elongated body and a slot in the fin, wherein the slot provides the retainer stop and allows the retainer to project further from the body when the body is bent in a first direction and the retainer stop prevents the retainer from settling back against the body when the body is bent in another direction. In yet other embodiments, the retainer stop is formed from the elongated body, and can move to a position between the retainer and the elongated body when the elongated body is bent in order to prevent the retainer from settling back against the elongated body.

The details of one or more aspects or embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

The details of one or more embodiments are set forth in the description below. Other features, objects and advantages will be apparent from the description, the drawings and the claims. The definition of several terms used herein include:

"Self-retaining system" refers to a self-retaining suture together with means for deploying the suture into tissue. Such deployment means include, without limitation, suture needles and other deployment devices as well as sufficiently rigid and sharp ends on the suture itself to penetrate tissue.

"Self-retaining suture" refers to a suture that may be a monofilament suture or a braided suture, and is positioned in tissue in two stages, namely deployment and affixation, and include at least one tissue retainer.

"Tissue retainer" (or simply "retainer" or "barb") refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction. As the tissue-penetrating end of each retainer moving through tissue during deployment faces away from the deployment direction (the direction of the passage of the suture during deployment), the tissue retainers should not catch or grab tissue during this phase. Once the self-retaining suture has been deployed, a force exerted in another direction, often substantially opposite to the deployment direction, to affix the suture in position causes retainers to be displaced from the retainers' deployment positions of resting substantially along the suture body and causes retainer ends to penetrate into the tissue resulting in tissue being caught between the retainer and the suture body. By way of example only, tissue retainer or retainers can include adhesive, chemical cross-linking, hooks, projections, barbs, darts, extensions, bulges, anchors, protuberances, spurs bumps points, cogs, tissue engagers, traction means, surface roughness, surface irregularities, surface defects edges, facets and the like.

"Retainer configurations" refers to configurations of tissue retainers and can include features such as size, shape, surface characteristics, and so forth. These are sometimes also referred to as "barb configurations".

"Fin" refers to the material and/or support structure that connects the retainer to the suture core or body.

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transitional segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition can be at about a midpoint or can be closer to one of the ends of the suture systems to form an "asymmetrical suture system."

"Suture thread" refers to the filamentary body component of the suture. The suture thread may be monofilamentary, or, multifilamentary.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially performed in a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as catgut, polyglycolic acid, lactic acid polymers, polyether-esters (e.g., copolymers of polyglycolide with polyglycols, polyglycolide with polyethers, polylactic acid with polyglycols or polylactic acid with polyethers), copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, 20040024169, and 20040116620. Degradable sutures can also include dissolvable sutures made of a dissolvable polymer, such as a polyvinyl alcohol partly deacetylated polymer, but not limited thereto. Sutures made from degradable suture material lose tensile strength as the material degrades.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyethylene terephthlate, polytetrafluoroethylene, polyether-ester (such as polybutylene or polyethylene terepthalate based copolymers with polyglycols or polyethers), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

Sutures materials are broadly classified as being degradable or bioabsorbable (i.e., they break down completely in the body over time), such as those composed of catgut, glycolic acid polymers and copolymers, lactic acid polymers and copolymers, and polyether-esters based copolymers such as polyglycolide or lactide copolymers with polyglycols or polyethers; or as being non-absorbable (permanent; nondegradable), such as those made of polyamide, polytetrafluoroethylene, polyethylene terephthalate, polyurethane, polyether-esters based copolymers such as polybutylene or polyethylene terephthalate with polyglycols or polyethers, metal alloys, metal (e.g., stainless steel wire), polypropylene, polyethelene, silk, and cotton. Degradable (bioabsorbable) sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses.

Bioabsorbable sutures can be made of materials which are broken down in tissue after a given period of time, which depending on the material can be from ten days to eight weeks. The sutures are used therefore in many of the internal tissues of the body. In most cases, three weeks is sufficient for the wound to close firmly. At that time the suture is not needed any more, and the fact that it disappears is an advantage, as there is no foreign material left inside the body and no need for the patient to have the sutures removed. In rare cases, bioabsorbable sutures can cause inflammation and be rejected by the body rather than absorbed. Bioabsorbable sutures were first made from the intestines of mammals. For example, gut sutures can be made of specially prepared bovine or ovine intestine, and can be untreated (plain catgut), tanned with chromium salts to increase the suture persistence in the body (chromic catgut), or heat-treated to give more rapid absorption (fast catgut). Concern about transmitting diseases such as bovine spongiform encephalopathy, has resulted in the gut being harvested from stock which have been tested to determine that the natural polymers used as suture materials do not carry viral diseases. Bioabsorbable sutures can be made of synthetic polymer fibers, which can be monofilaments or braided.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to deployment means such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which generally is then deformed to a final shape to hold the suture and needle together. As such, atraumatic needles do not require extra time on site for threading and the suture end at the needle attachment site is generally smaller than the needle body. In the traumatic needle the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles would are preferred.

Suture needles may also be classified according to the needle point geometry. For example, needles may be (i) "tapered" whereby the needle body is round and tapers smoothly to a point; (ii) "cutting" whereby the needle body is triangular and has sharpened cutting edge on the inside; (iii) "reverse cutting" whereby the cutting edge is on the outside; (iv) "trocar point" or "tapercut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and 5,464,422 (W.L. Gore, Newark, Del.); and 5,941,899; 5,425,746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

'Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects achieve a downward pull on this tissue and the underlying ligaments, and fat descends into the plane between the superficial and deep facial fascia, thus allowing facial tissue to sag. Face-lift procedures are designed to lift these sagging tissues, and are one example of a more general class of medical procedure known as a tissue elevation procedure. More generally, a tissue elevation procedure reverses the appearance change that results from gravitation effects over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing or replacing damaged or diseased organs and tissues. While normally composed of biologically compatible synthetic materials (e.g., medical-grade stainless steel, titanium and other metals, or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopaedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

As mentioned above, despite the multitude of advantages of self-retaining sutures, there remains a need and desire to improve upon the design of such sutures so that a variety of common limitations can be eliminated. For example, retainers formed by cutting into a suture body have a tendency to sometimes lie flat, i.e., not stand up or fan out as desired. Additionally, many existing techniques (e.g., cutting techniques) for manufacturing self-retaining sutures may reduce the tensile strength of the suture, as explained below. Other issues exist with the current manufacturing methods. These include the fact that barbs cut and bent into a certain angle of elevation may relax to a less prone position post-manufacturing (during sterilization, attachment, etc.) and prior to implantation due to the residual stresses in the suture material and/or viscoelastic effects. This may decrease the effectiveness of the self-retaining suture when used to close a wound.

Figure 1A:
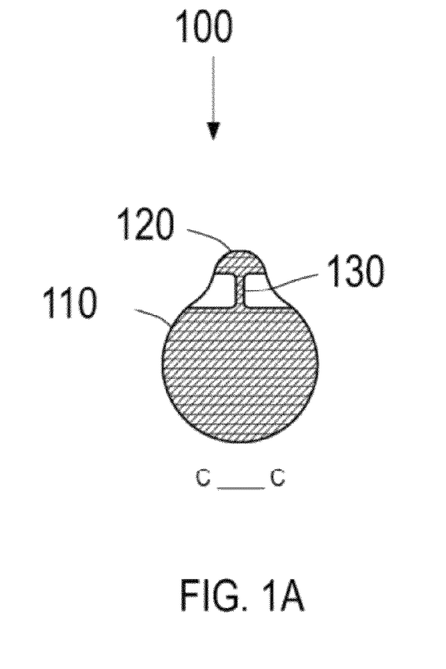
FIG. 1A shows a cross-sectional view of an embodiment of the invention, where a retainer is pinched from the self-retaining sutures core.
Figure 1B:
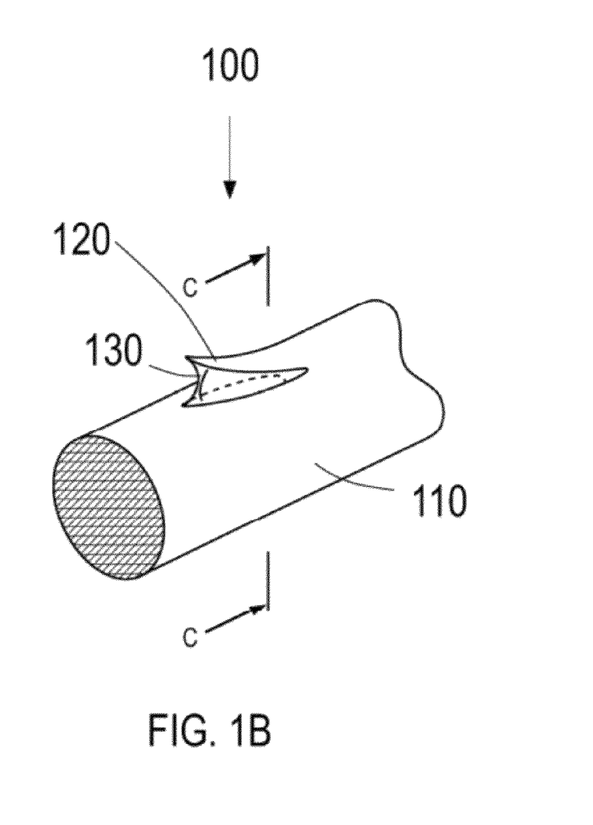
FIG. 1B shows a perspective view of the pinched suture producing the retainer.

In an embodiment of the invention, a self-retaining suture with retainers allows passage of the suture in one direction, but inhibits movement of the suture in the opposite direction, wherein the retainers minimally impact the integrity and strength of the suture. As shown in FIG. 1, in an embodiment of the invention, the self-retaining suture 100 has one or more retainers 120 formed by squeezing or pinching or otherwise deforming the suture core or thread body 110 and causing the retainer 120 to form out of the deformed material drawn from the suture core or thread body 110. Generally, it is believed that the fin 130 formed by such squeezing will be plastically deformed as well as the bottom of the retainer that is connected to the fin. One advantage of forming a retainer by pinching the suture core or thread body is that it can be easy to form. In this embodiment of the invention, the retainers are formed by squeezing or otherwise deforming a part of the suture and causing the retainer to form out of deformed material drawn from the suture core. An advantage of this method of retainer forming is the supporting fin that is left underneath the retainer in order to prevent the barb from laying down flat. In various embodiments of the invention, the width and length of a fin 130, formed between the retainer 120 and the core 110, can be controlled by adjusting the speed with which the suture core or body 110 passes through a squeezing tool, the shape of the squeezing tool, the frequency of application and withdrawal of the squeezing tool and the pressure applied by the squeezing tool.

Figure 2A:
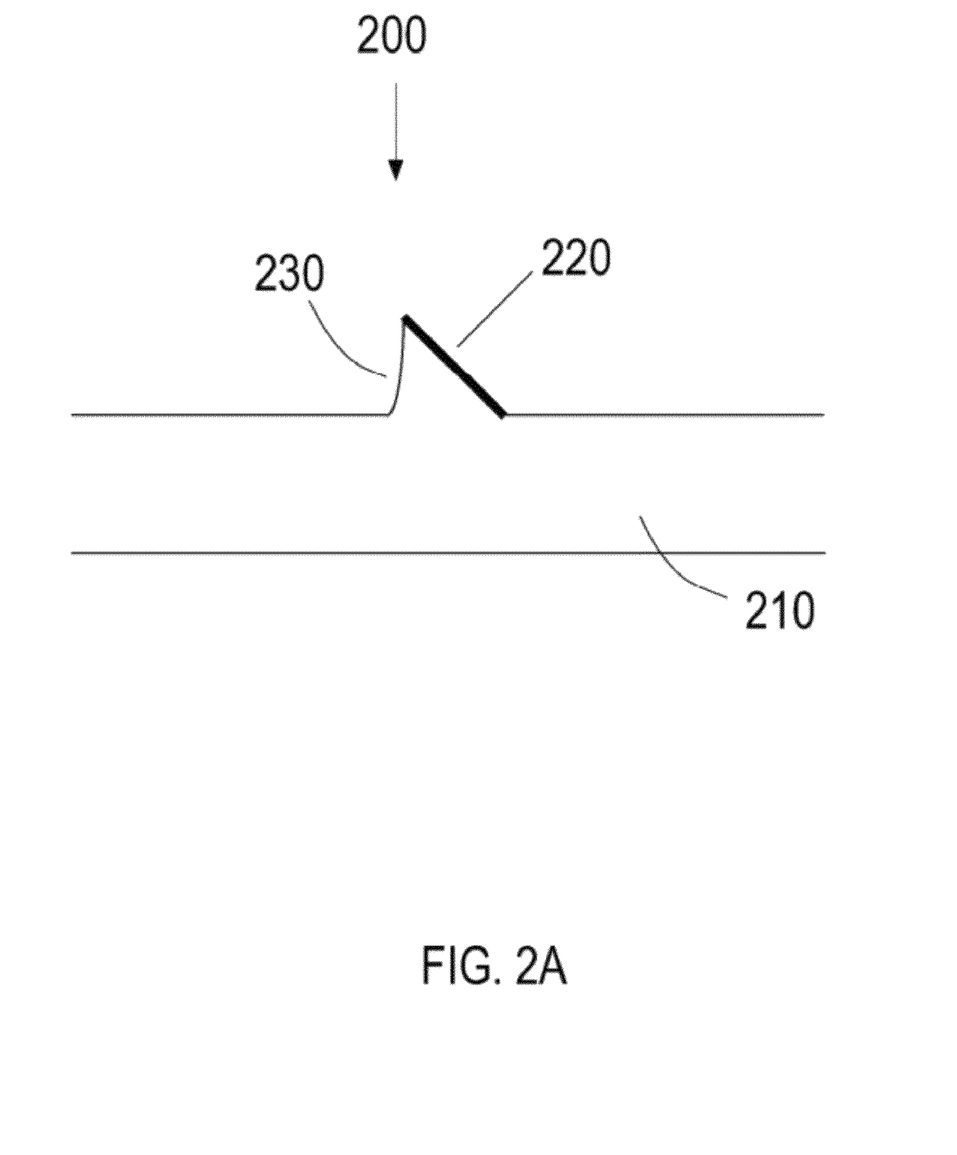
FIG. 2A shows a profile view of the pinched suture producing the retainer.
Figure 2B:
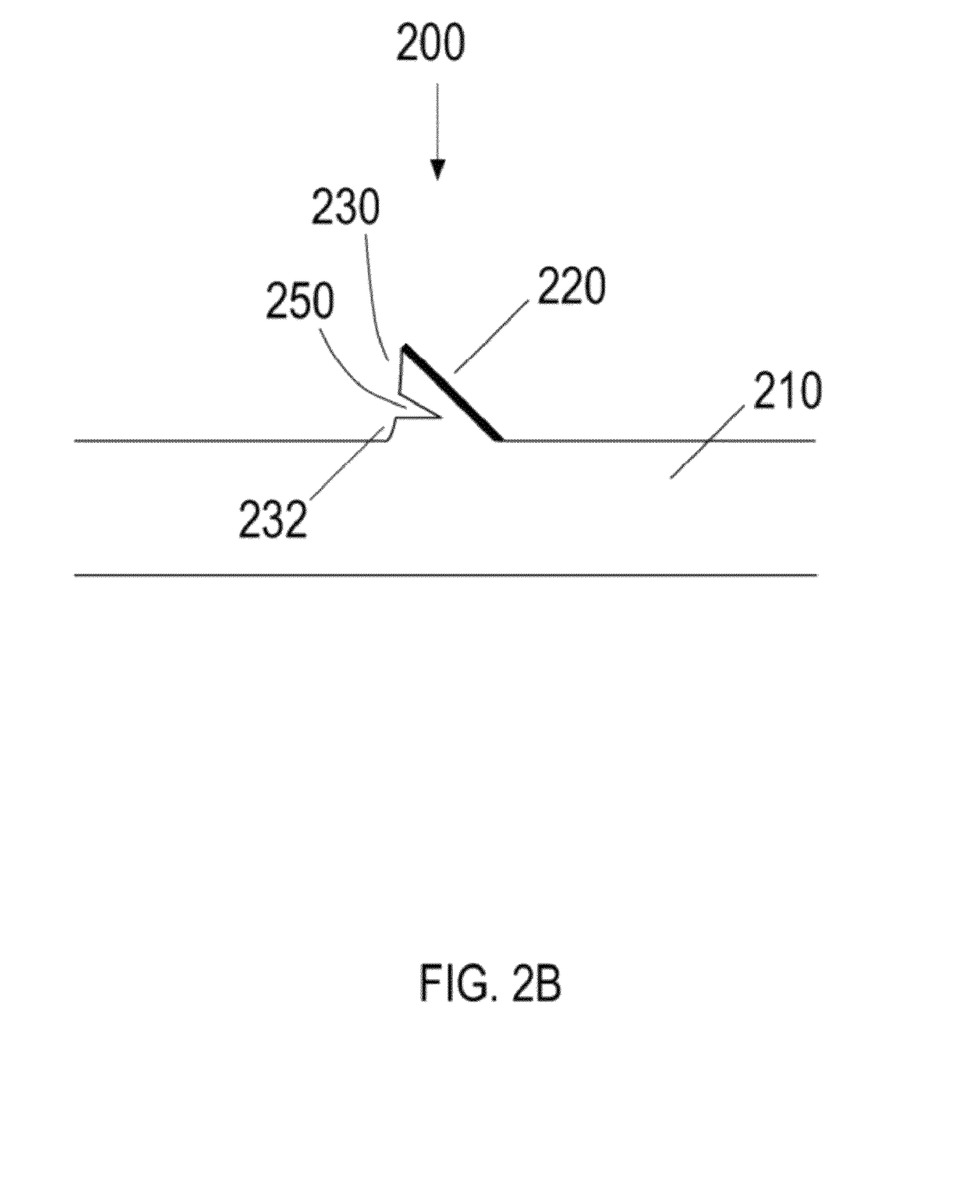
FIG. 2B shows a profile view of the pinched suture producing the retainer with a cut in the fin.
Figure 2C:
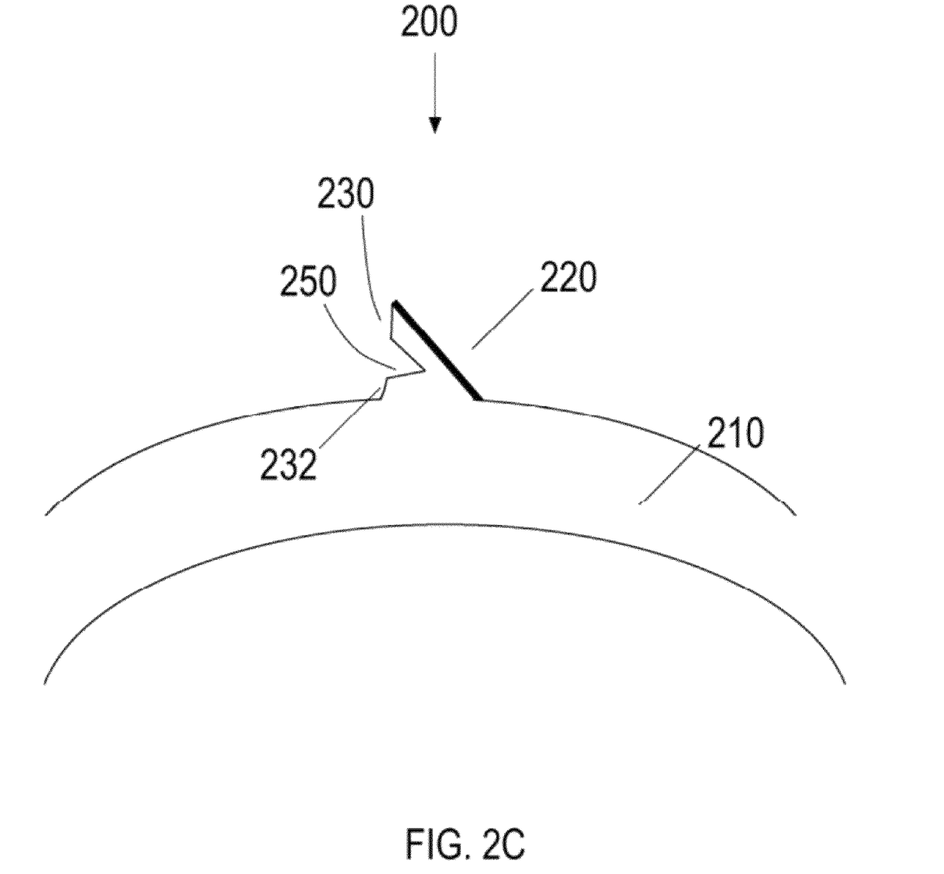
FIG. 2C shows a profile view of the pinched suture producing the retainer with a cut in the fin with the suture bent away from the retainer.
Figure 2D:
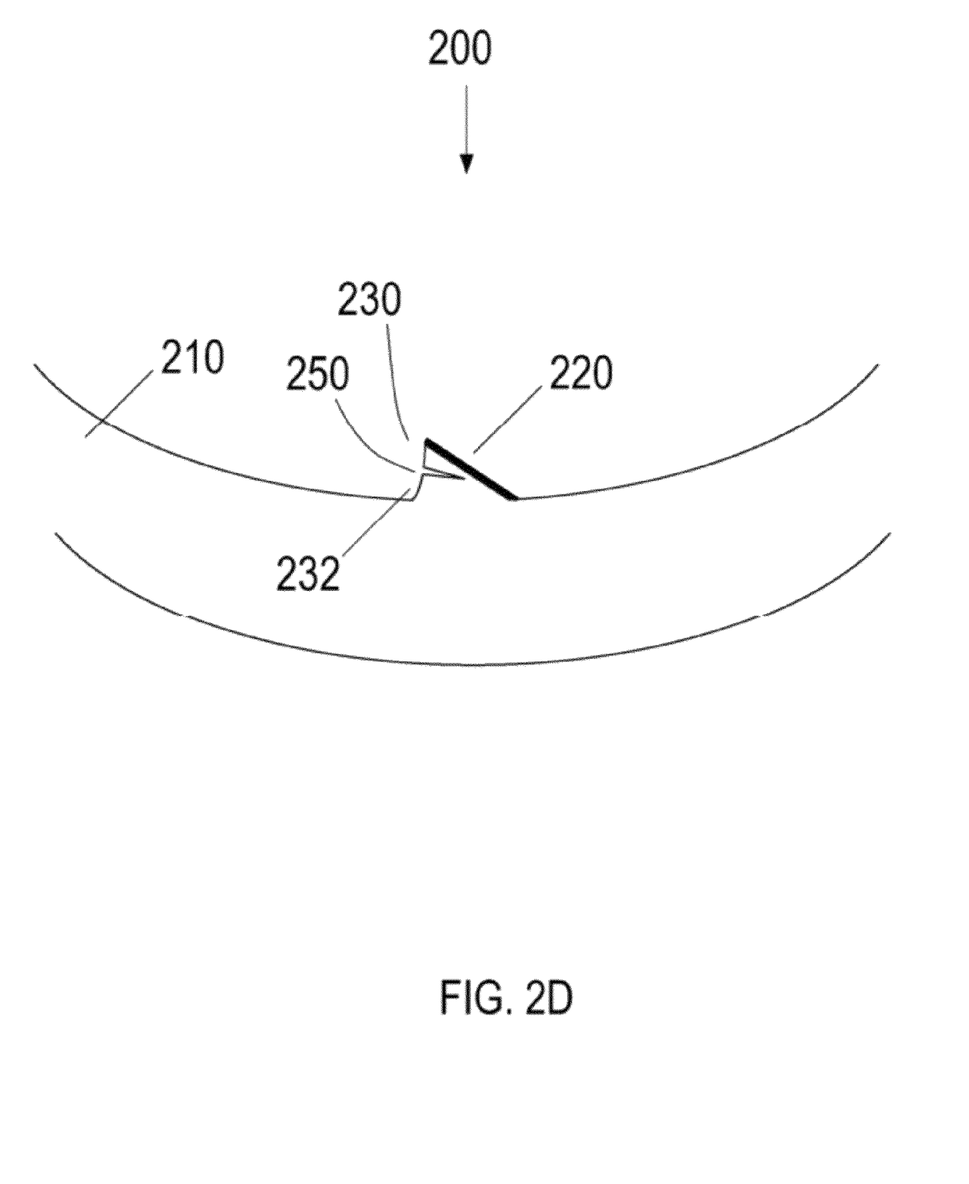
FIG. 2D shows a profile view of the pinched suture producing the retainer with a cut in the fin when the suture is bent toward from the retainer.

In various embodiments of the invention, after the suture core or body 210 is squeezed or otherwise deformed to form the retainer 220, a cut can be made in the fin 230, reducing the amount of material under the retainer 220 (see FIG. 2B). The cut in the fin 230, minimizes the impediment of the fin 230 in allowing the suture 200 with retainer 220 to be inserted into the tissue and allows for better fixation in the tissues once inserted. FIGS. 2A-FIG. 2E show profile views of sutures 200 according to various embodiments of the invention. FIG. 2A depicts a side view of a suture 200 that has been squeezed or otherwise formed by deformation of the suture core or body 210 in order to produce one or more retainers or barbs such as retainer 220 and a fin 230 which supports and spaces the retainer 220 from the core or body 210. It is to be understood that such a suture can have a multiplicity of retainers 220 so formed or deformed from the core 210 and located at various positions along the length of the core 210. FIG. 2B to FIG. 2D depict a suture 200 that is the suture 200 as depicted in FIG. 2A with the addition of a cut or slot 250 formed in the fin 230. The cut may be formed by a number of techniques including using a blade to form the cut after the fin and retainer is formed, and also by using a squeezing or deforming tool that simultaneously formed the fin and retainer and also the cut in the fin. The cut or slot 250 in the fin can be made with a simple cut or may be made by the removal of, for example, a wedge shaped section from the fin as depicted in FIG. 2B.

FIG. 2C depicts the embodiment of FIG. 2B with the suture curved outwardly with respect to the retainer 220, such that the retainer 220 projects more prominently from the core 210 and the inferior or base fin portion 232 located below the cut and the superior fin portion 230 located above the cut. As is evident from FIG. 2C the area of the cut has been enlarged due to the projection of the retainer 220 further away from the core 210 of the suture 200. FIG. 2D depicts the embodiment of FIG. 2B with the suture curved inwardly with respect to the retainer, such that the retainer 220 projects less prominently from the core 210 as for example compared with FIG. 2B. It is noted that due to the remaining material of the fin and in particular the inferior or base fin portion 232 located below the cut and the superior fin portion 230 located above the cut, with the suture curved inwardly, the retainer does not settle back into the core of the suture, but maintains a prominence and projection above the core of the suture. The base fin portion 232 accordingly acts as a stop ensuring that the retainer does not settle back into the core 210. Accordingly, even with the suture curved inwardly as depicted in FIG. 2D, the retainer is prominent enough to engage tissue when the suture is for example pulled in a direction opposite to the direction of the initial deployment of the suture in the tissue.

Figure 3A:
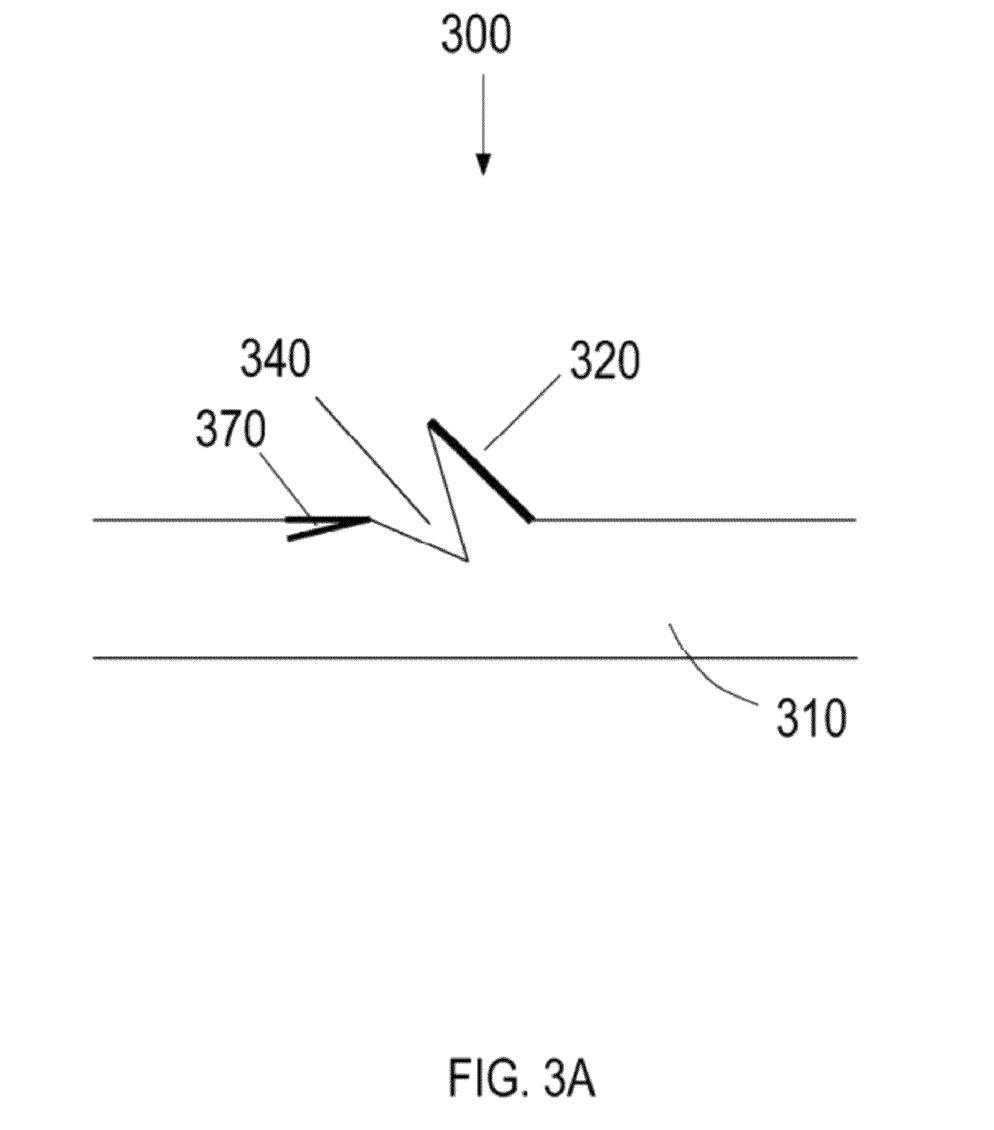
FIG. 3A shows a profile view of a suture with a first retainer and a recess associated with cutting the retainer.
Figure 3B:
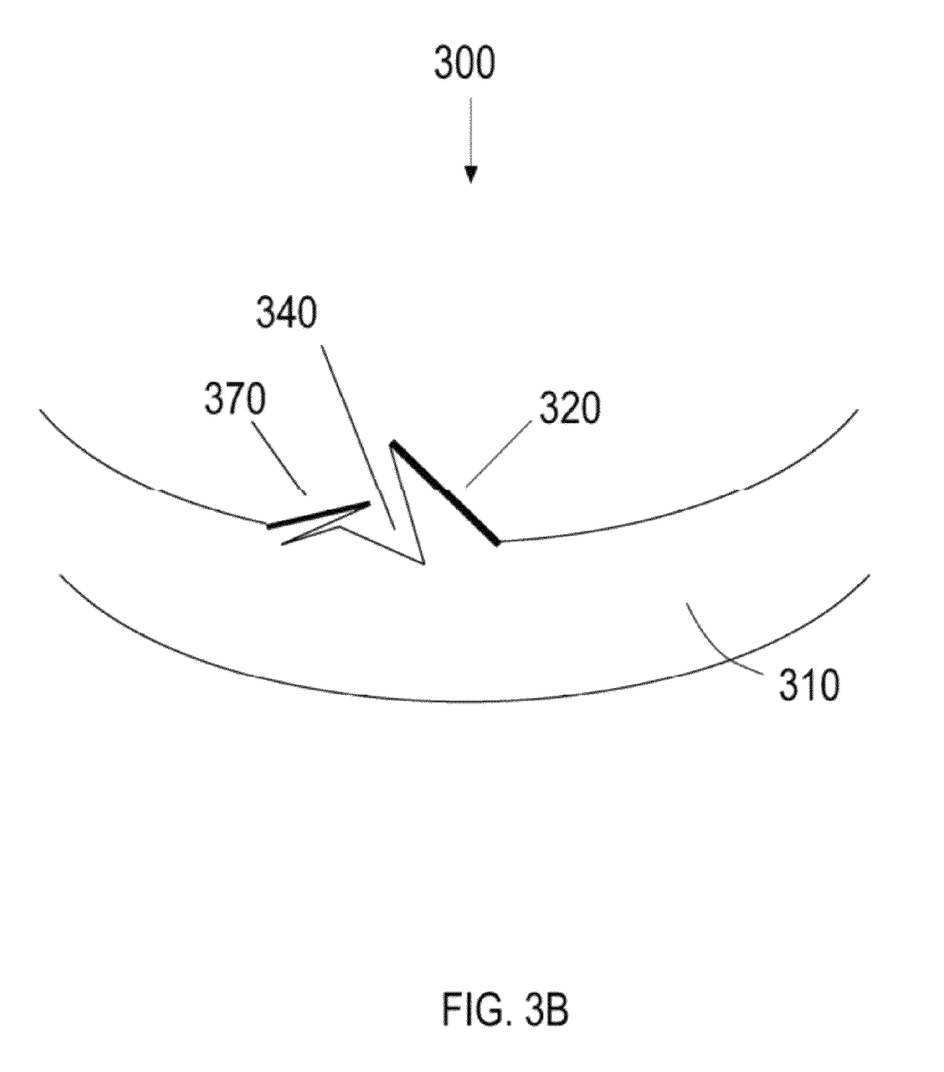
FIG. 3B shows a profile view of an element cut into the suture to stop the retainer from being compressed back into a recess.

Another embodiment of the suture 300 of the invention is depicted in FIG. 3A and FIG. 3B. In FIG. 3A, a retainer 320 is formed in the suture core 310 by for example cutting the retainer into the core 310. Additionally adjacent to the retainer 320, a retainer stopper 330 is formed in the core 310. In this embodiment the retainer stop 370 can be formed with a cutting technique that involves cutting the core 320 in a direction opposite to the cut which was made to form the retainer 320. As depicted in FIG. 3B when the suture is curved inwardly with respect to the retainer, the retainer stopper 370 projects to a position below the retainer 320 and prevents or stops the retainer 320 from settling back into the core 310. Accordingly, even with the suture curved inwardly as depicted in FIG. 3B, the retainer is prominent enough to engage tissue when the suture is for example pulled in a direction opposite to the direction of the initial deployment of the suture in the tissue.

In various embodiments of the invention, incisions are cut into the fin using metal blades, sapphire blades, heating applied prior to cutting, heating applied during cutting and heating applied after cutting. In various embodiments of the invention, cuts into the fin vary in size, shape and angle of cut parameters so that the retainer can not be folded back against the core of the suture. In various embodiments of the invention, the cut is made using size, shape and angle of cut parameters so that the retainer strength is not diminished.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A self-retaining suture comprising:
   one or more filaments wherein the one or more filaments have an elongated body;
   one or more tissue retainers formed by applying pressure to the elongated body such that the tissue retainers protrude outward from the elongated body; and
   one or more fins, wherein each fin corresponds with the area of the elongated body where the pressure was applied and said one or more fins are located between one or more respective tissue retainers and the elongated body, and supports the respective one or more retainers
   wherein a wedge shaped section has been cut from the fin to provide a cut fin, said cut fin comprising an inferior fin portion located below the cut between the cut and the elongated body, and a superior fin portion located above the cut between the cut and the tissue retainer.

2. The self-retaining suture of claim 1, wherein the pressure applied pinches the elongated body to form the retainer.

3. The self-retaining suture of claim 1, wherein the fin holds the retainer in position.

4. The self-retaining suture of claim 1, wherein the cut fin holds the retainer in position while allowing some movement.

5. The self-retaining suture of claim 1, wherein the cut fin allows the tissue retainer to compress toward the suture body during insertion of the suture into tissue.

* * * * *